US012360191B2

(12) United States Patent
Kutsuna (10) Patent No.: US 12,360,191 B2
(45) Date of Patent: Jul. 15, 2025

(54) DATA PROCESSING DEVICE, MAGNETIC RESONANCE IMAGING APPARATUS, AND DATA PROCESSING METHOD

(71) Applicant: CANON MEDICAL SYSTEMS CORPORATION, Tochigi (JP)

(72) Inventor: Hideaki Kutsuna, Kawasaki (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 153 days.

(21) Appl. No.: 18/048,503

(22) Filed: Oct. 21, 2022

(65) Prior Publication Data

US 2023/0130481 A1    Apr. 27, 2023

(30) Foreign Application Priority Data

Oct. 21, 2021   (JP) .................................. 2021-172657

(51) Int. Cl.
  *G01R 33/56*   (2006.01)
  *G06N 3/045*   (2023.01)

(52) U.S. Cl.
  CPC ......... *G01R 33/5608* (2013.01); *G06N 3/045* (2023.01)

(58) Field of Classification Search
  CPC .......................... G06N 3/045; G01R 33/5608
  See application file for complete search history.

(56) References Cited

U.S. PATENT DOCUMENTS

| 10,922,393 | B2  |     | 2/2021  | Spizhevoy et al. |
|------------|-----|-----|---------|------------------|
| 11,200,982 | B2  | *   | 12/2021 | Chen ............ G06N 3/088 |
| 2018/0018451 | A1 |   | 1/2018  | Spizhevoy et al. |
| 2019/0378270 | A1 |   | 12/2019 | Ida et al. |
| 2020/0022607 | A1 |   | 1/2020  | Pratt et al. |
| 2020/0202999 | A1 | * | 6/2020  | Takeshima ............ G16H 50/20 |
| 2021/0110020 | A1 |   | 4/2021  | Spizhevoy et al. |
| 2022/0254021 | A1 |   | 8/2022  | Ida et al. |
| 2022/0414837 | A1 | * | 12/2022 | Kaneko ................. G06T 7/0012 |

FOREIGN PATENT DOCUMENTS

| JP | 2019-525325 A | 9/2019 |
|----|---------------|--------|
| JP | 2020-505179 A | 2/2020 |

OTHER PUBLICATIONS

Extended European Search Report issued Feb. 24, 2023, in European Patent Application No. 22202854.0, 12 pages.

* cited by examiner

*Primary Examiner* — Gregory H Curran (74) *Attorney, Agent, or Firm* — Oblon, McClelland, Maier & Neustadt, L.L.P.

(57) ABSTRACT

A data processing device according to an embodiment includes a processing circuit. The processing circuit performs data processing using a learned model with a neural network including a division processing layer that divides input complex first vector data by complex second vector data containing features of the first vector data, a nonlinear layer that is disposed in the subsequent stage of the division processing layer and that performs a nonlinear operation, and a multiplication processing layer that is disposed in the subsequent stage of the nonlinear layer and that multiplies the input data by the second vector data.

19 Claims, 7 Drawing Sheets

DATA PROCESSING DEVICE, MAGNETIC RESONANCE IMAGING APPARATUS, AND DATA PROCESSING METHOD

CROSS-REFERENCE TO RELATED APPLICATIONS

This application is based upon and claims the benefit of priority from Japanese Patent Application No. 2021-172657, filed on Oct. 21, 2021; the entire contents of which are incorporated herein by reference.

FIELD

Embodiments described herein relate generally to a data processing device, a magnetic resonance imaging apparatus, and a data processing method.

BACKGROUND

In machine learning using a neural network, a real-valued neural network is used as a standard.

However, in the medical data processing device such as a magnetic resonance imaging apparatus and an ultrasonic diagnostic device, signal processing using complex numbers is often used. Hence, various applications are possible by using a complex-valued neural network.

In this example, for example, in a medical image such as a magnetic resonance image and an ultrasonic image, while the phase information of an image, for example, the gradient of the phase, is often important, the absolute value of the phase seldom has significant implications. For example, in the magnetic resonance imaging apparatus, a slight difference in the center frequency appears as a phase modulation of the entire image. However, in many cases, the importance of the absolute values of the phases is relatively low.

Thus, for example, when the complex-valued neural network is applied to a medical image for noise removal, region extraction, and the like, it is desirable to configure the neural network such that the output result does not vary significantly with respect to the phase modulation of the entire image, while the phase information of the input image is not ignored.

DETAILED DESCRIPTION

A data processing device provided in one aspect of the present invention includes a processing circuit. The processing circuit performs data processing using a learned model with a neural network that includes a division processing layer that divides input complex first vector data by complex second vector data containing the features of the first vector data, a nonlinear layer that is disposed in the subsequent stage of the division processing layer and that performs a nonlinear operation, and a multiplication processing layer that is disposed in the subsequent stage of the nonlinear layer and that multiplies the input data by the second vector data.

First Embodiment

Hereinafter, a data processing device, a magnetic resonance imaging apparatus, and a data processing method according to an embodiment will be described in detail with reference to the accompanying drawings.

Figure 1:
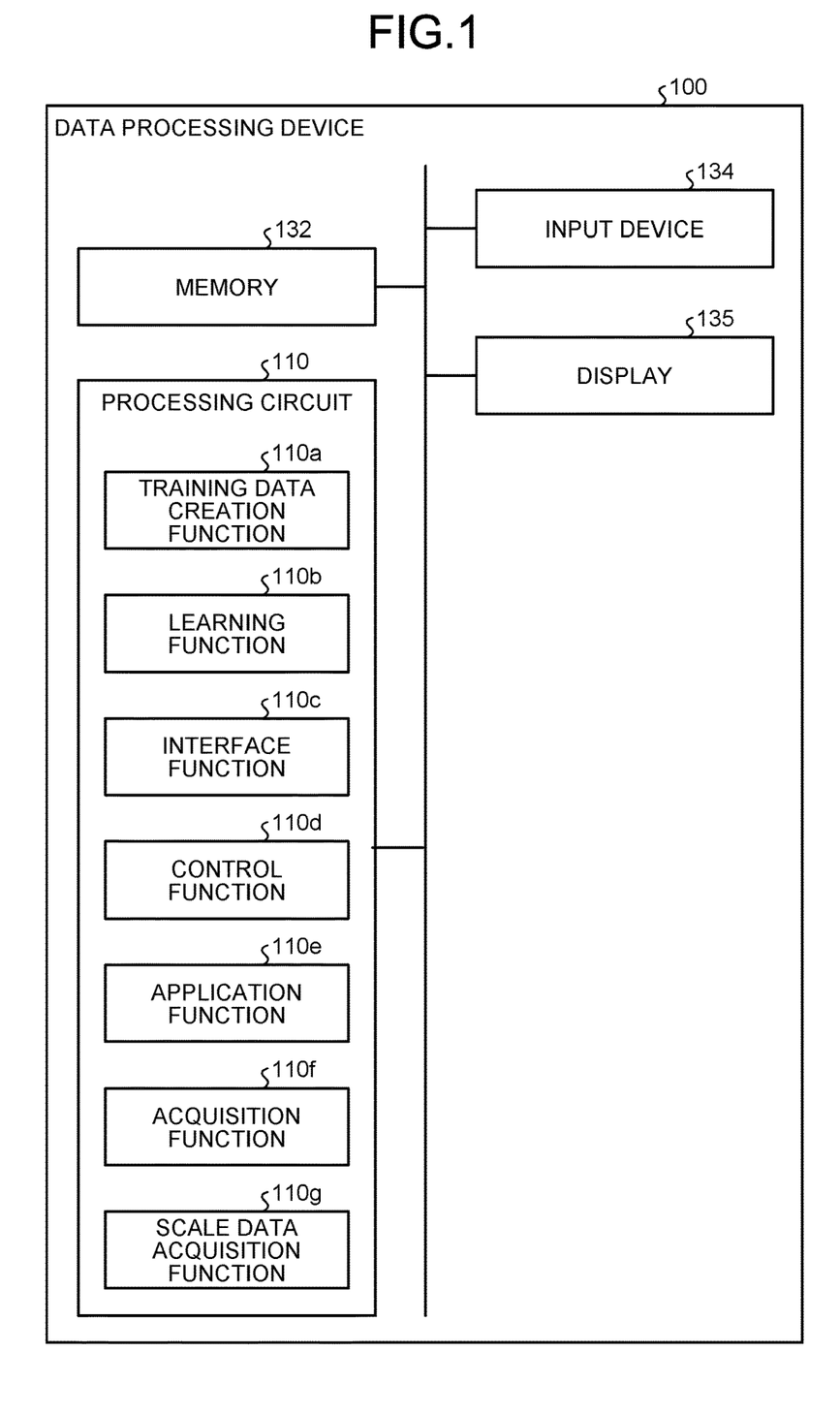
FIG. 1 is a diagram illustrating an example of a data processing device according to an embodiment.

With reference to FIG. 1, a configuration of a data processing device 100 according to the embodiment will be described.

The data processing device 100 is a device that generates data using machine learning. For example, the data processing device 100 is connected to various medical image diagnostic devices such as the magnetic resonance imaging apparatus illustrated in FIG. 2 and the ultrasonic diagnostic device illustrated in FIG. 3. The data processing device 100 performs processing such as processing a signal received from the medical image diagnostic device, generating a learned model, and executing the learned model. Examples of the medical image diagnostic device to which the data processing device 100 is connected are not limited to the magnetic resonance imaging apparatus and the ultrasonic diagnostic device, but may also be other devices such as an X-ray CT device and a PET device.

The data processing device 100 is typically a medical data processing device that processes medical data. However, in the embodiment, the data processing device 100 is not limited to the medical data processing device. As an example, the data processing device 100 may be a device for processing magnetic resonance data that is not medical data.

The data processing device 100 includes a processing circuit 110, a memory 132, an input device 134, and a display 135. The processing circuit 110 includes a training data generation function 110a, a learning function 110b, an interface function 110c, a control function 110d, an application function 110e, an acquisition function 110f, and a scale data acquisition function 110g.

In the embodiment, each processing function performed by the training data generation function 110a, the learning function 110b, the interface function 110c, the control function 110d, the application function 110e, the acquisition function 110f, and the scale data acquisition function 110g, and a learned model (for example, a neural network) are stored in the memory 132 in the form of computer executable programs. The processing circuit 110 is a processor that implements a function corresponding to each computer program, by reading a computer program from the memory 132 and executing the computer program. In other words, the processing circuit 110 in a state in which each computer program is read has each function illustrated in the processing circuit 110 in FIG. 1. Moreover, the processing circuit 110 in a state in which a computer program corresponding to a learned model (neural network) is read can perform the processing according to the learned model. In FIG. 1, the functions of the processing circuit 110 are implemented by a single processing circuit. However, the functions of the processing circuit 110 may also be implemented by configuring the processing circuit 110 by combining a plurality of independent processors, and causing each of the processors to execute a computer program. In other words, each of the functions described above may be configured as a computer program, and a single processing circuit may execute each computer program. Moreover, a single processing circuit may implement two or more functions of the processing circuit 110. As another example, a specific function may be implemented in a dedicated independent program execution circuit.

In FIG. 1, the processing circuit 110, the training data generation function 110a, the learning function 110b, the interface function 110c, the control function 110d, the application function 110e, the acquisition function 110f, and the scale data acquisition function 110g are examples of a processing unit, a generation unit, an input unit (learning unit), a reception unit, a control unit, an application unit, an acquisition unit, and a scale data acquisition unit, respectively.

For example, the term "processor" used in the above description refers to a central processing unit (CPU), a graphical processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processor implements the function by reading and executing a computer program stored in the memory 132.

Moreover, instead of storing a computer program in the memory 132, the computer program may also be directly incorporated in a circuit of the processor. In this case, the processor implements the function by reading and executing a computer program incorporated in the circuit. Thus, for example, instead of storing a learned model in the memory 132, a computer program according to the learned model may be directly incorporated in the circuit of the processor.

When the processing circuit 110 is incorporated in various medical image diagnostic devices, or when the processing is performed in conjunction with various medical image diagnostic devices, the processing circuit 110 may also have a function that can execute the process associated with the above.

With the training data generation function 110a, the processing circuit 110 generates training data for learning, on the basis of the data and images acquired by the interface function 110c.

With the learning function 110b, the processing circuit 110 generates a learned model, by performing learning using the training data generated by the training data generation function 110a. With the interface function 110c, the processing circuit 110 acquires the data, images, and the like for image generation by the application function 110e, from the memory 132.

With the control function 110d, the processing circuit 110 controls the overall processing of the data processing device 100. More specifically, with the control function 110d, the processing circuit 110 controls the processing of the processing circuit 110, on the basis of various setting requests input from an operator via the input device 134, and various control programs and various types of data read from the memory 132.

Moreover, with the application function 110e, the processing circuit 110 generates an image on the basis of the results of processing performed using the training data generation function 110a and the learning function 110b. Furthermore, with the application function 110e, the processing circuit 110 applies the learned model generated by the learning function 110b to an input image, and generates an image on the basis of the application results of the learned model. Still furthermore, with the acquisition function 110f, the processing circuit 110 acquires various types of data. Still furthermore, with the scale data acquisition function 110g, the processing circuit 110 acquires scale data, which will be described below.

The memory 132 includes a semiconductor memory element such as a random access memory (RAM) and a flash memory, a hard disk, an optical disc, and the like. The memory 132 is a memory that stores data such as image data for display generated by the processing circuit 110, and image data for training. The memory 132 stores various types of data such as a control program for image processing and display processing, as necessary.

The input device 134 receives various instructions and information input by the operator. For example, the input device 134 is a pointing device such as a mouse or a trackball, a selection device such as a mode change-over switch, or an input device such as a keyboard.

Under the control of the control function 110d and the like, the display 135 displays a graphical user interface (GUI) for receiving an input of imaging conditions, an image generated by the control function 110d, and the like. For example, the display 135 is a display device such as a liquid crystal display. The display 135 is an example of a display unit. The display 135 includes a mouse, a keyboard, a button, a panel switch, a touch command screen, a foot switch, a trackball, a joystick, and the like.

Figure 2:
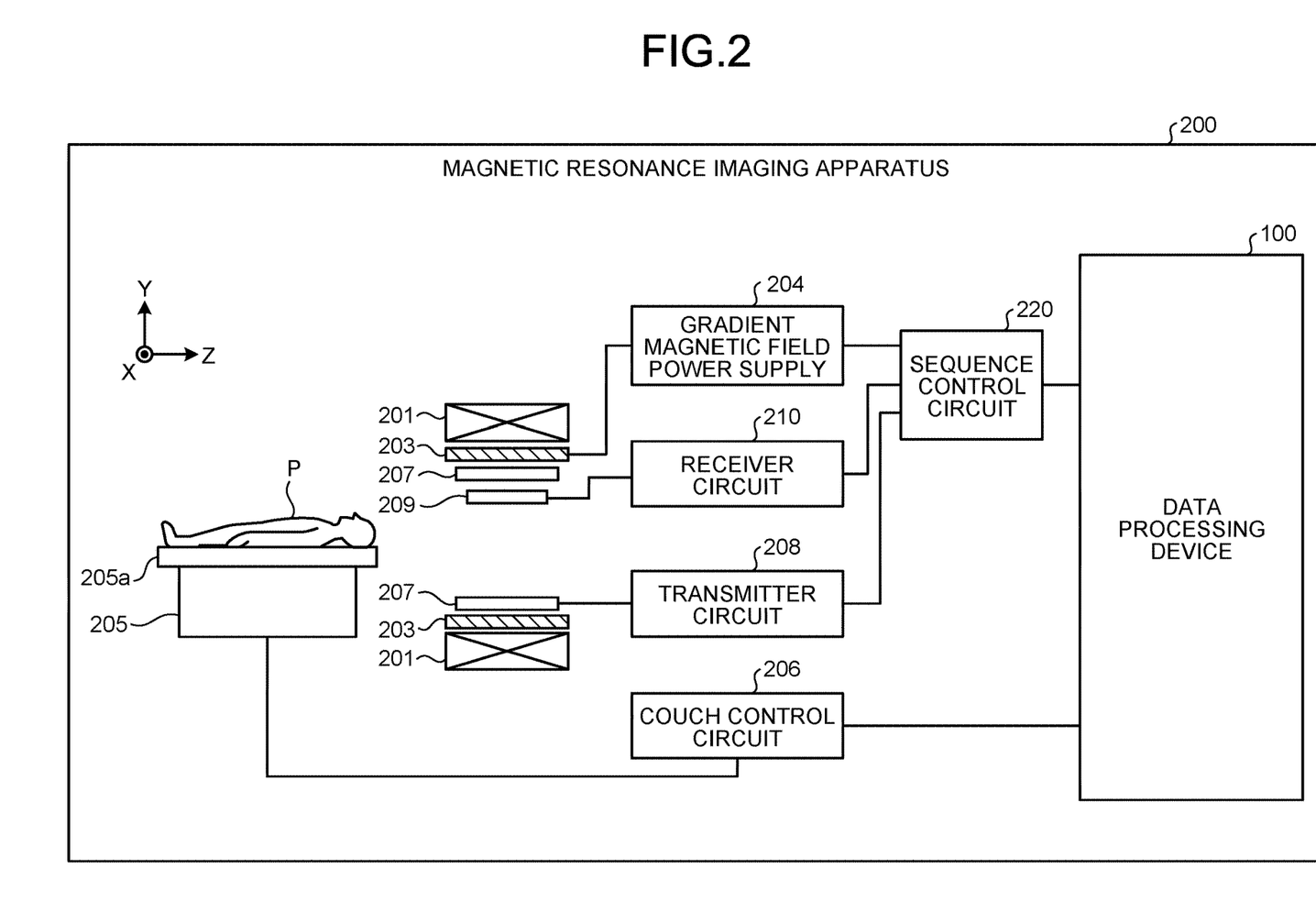
FIG. 2 is a diagram illustrating an example of a magnetic resonance imaging apparatus according to the embodiment.

FIG. 2 is an example of a magnetic resonance imaging apparatus 200 incorporated with the data processing device 100 according to the embodiment.

As illustrated in FIG. 2, the magnetic resonance imaging apparatus 200 includes a static magnetic field magnet 201, a static magnetic field power supply (not illustrated), a gradient coil 203, a gradient magnetic field power supply 204, a couch 205, a couch control circuit 206, a transmitter coil 207, a transmitter circuit 208, a receiver coil 209, a receiver circuit 210, a sequence control circuit 220 (sequence control unit), and the data processing device 100 described in FIG. 1. The magnetic resonance imaging apparatus 200 does not include a subject P (for example, human body). Moreover, the configuration illustrated in FIG. 2 is merely an example.

The static magnetic field magnet 201 is a magnet formed in a substantially hollow cylindrical shape, and generates a static magnetic field in the interior space. For example, the static magnetic field magnet 201 is a superconducting magnet and the like, and is excited by receiving supply of electric current from the static magnetic field power supply. The static magnetic field power supply supplies electric current to the static magnetic field magnet 201. As another example, the static magnetic field magnet 201 may also be a permanent magnet. In this case, the magnetic resonance imaging apparatus 200 need not be equipped with a static magnetic field power supply. Moreover, the static magnetic field power supply may be provided separately from the magnetic resonance imaging apparatus 200.

The gradient coil 203 is a coil formed in a substantially hollow cylindrical shape, and is placed inside the static magnetic field magnet 201. The gradient coil 203 is formed by combining three coils corresponding to X, Y, and Z axes that are orthogonal to each other. These three coils individually receive electric current from the gradient magnetic field power supply 204, and generate gradient magnet fields in which the magnetic field intensity changes along the X, Y, and Z axes. For example, the gradient magnetic fields of the X, Y, and Z axes generated by the gradient coil 203 are a slice gradient magnetic field Gs, a phase encoding gradient magnetic field Ge, and a readout gradient magnetic field Gr. The gradient magnetic field power supply 204 supplies electric current to the gradient coil 203.

The couch 205 includes a couchtop 205a on which the subject P is placed. Under the control of the couch control circuit 206, while the subject P is placed thereon, the couchtop 205a is inserted into the cavity (imaging port) of the gradient coil 203. In general, the couch 205 is installed so that the longitudinal direction is parallel to the center axis of the static magnetic field magnet 201. Under the control of the data processing device 100, the couch control circuit 206 moves the couchtop 205a in the longitudinal direction and the vertical direction, by driving the couch 205.

The transmitter coil 207 is placed inside the gradient coil 203, and a high-frequency magnetic field is generated by receiving the supply of RF pulses from the transmitter circuit 208. The transmitter circuit 208 supplies RF pulses corresponding to the Larmor frequency that is determined by the type of target atom and the magnetic field intensity, to the transmitter coil 207.

The receiver coil 209 is placed inside the gradient coil 203 to receive a magnetic resonance signal (hereinafter, referred to as an "MR signal" as necessary) emitted from the subject P under the influence of a high-frequency magnetic field. Upon receiving the magnetic resonance signal, the receiver coil 209 outputs the received magnetic resonance signal to the receiver circuit 210.

The transmitter coil 207 and the receiver coil 209 described above are merely examples. The transmitter coil 207 and the receiver coil 209 may be configured by combining one or a plurality of a coil equipped only with a transmission function, a coil equipped only with a reception function, and a coil equipped with transmission and reception functions.

The receiver circuit 210 detects the magnetic resonance signal output from the receiver coil 209, and generates magnetic resonance data on the basis of the detected magnetic resonance signal. More specifically, the receiver circuit 210 generates magnetic resonance data by digitally converting the magnetic resonance signal output from the receiver coil 209. Moreover, the receiver circuit 210 transmits the generated magnetic resonance data to the sequence control circuit 220. The receiver circuit 210 may also be provided on the side of the gantry device including the static magnetic field magnet 201, the gradient coil 203, and the like.

On the basis of sequence information, the sequence control circuit 220 drives the gradient magnetic field power supply 204, the transmitter circuit 208, and the receiver circuit 210 to capture images of the subject P. In this example, the sequence information is information that defines the procedure for imaging. In the sequence information, the intensity of electric current supplied to the gradient coil 203 by the gradient magnetic field power supply 204 and the timing at which the electric current is supplied, the intensity of the RF pulse supplied to the transmitter coil 207 by the transmitter circuit 208 and the timing at which the RF pulse is applied, and the timing at which the magnetic resonance signal is detected by the receiver circuit 210, and the like are defined. For example, the sequence control circuit 220 is an integrated circuit such as an application specific integrated circuit (ASIC) and a field programmable gate array (FPGA), and an electronic circuit such as a central processing unit (CPU) and a micro processing unit (MPU). The sequence control circuit 220 is an example of a scanning unit.

Moreover, upon receiving magnetic resonance data from the receiver circuit 210 as a result of capturing an image of the subject P by driving the gradient magnetic field power supply 204, the transmitter circuit 208, and the receiver circuit 210, the sequence control circuit 220 transfers the received magnetic resonance data to the data processing device 100. In addition to the processing described in FIG. 1, the data processing device 100 performs the overall control of the magnetic resonance imaging apparatus 200.

Returning to FIG. 1, the processing performed by the data processing device 100 and that is different from the processing described in FIG. 1 will be described. With the interface function 110c, the processing circuit 110 transmits sequence information to the sequence control circuit 220, and receives magnetic resonance data from the sequence control circuit 220. Moreover, upon receiving the magnetic resonance data, the processing circuit 110 with the interface function 110c stores the received magnetic resonance data in the memory 132.

With the control function 110d, the magnetic resonance data stored in the memory 132 is disposed in k-space. As a result, the memory 132 stores the k-space data.

The memory 132 stores the magnetic resonance data received by the processing circuit 110 with the interface function 110c, the k-space data disposed in the k-space by the processing circuit 110 with the control function 110d, image data generated by the processing circuit 110 with the generation function (or the application function 110e), and the like.

With the control function 110d, the processing circuit 110 performs the overall control of the magnetic resonance imaging apparatus 200, and controls imaging, the generation of an image, the display of the image, and the like. For example, the processing circuit 110 with the control function 110d receives an input of imaging conditions (imaging parameters and the like) on the GUI, and generates sequence information according to the received imaging conditions. Moreover, the processing circuit 110 with the control function 110d transmits the generated sequence information to the sequence control circuit 220.

With the generation function not illustrated in FIG. 1 (or the application function 110e), the processing circuit 110 generates a magnetic resonance image, by reading the k space data from the memory 132 and applying reconstruction processing such as Fourier transform on the read k space data.

Figure 3:
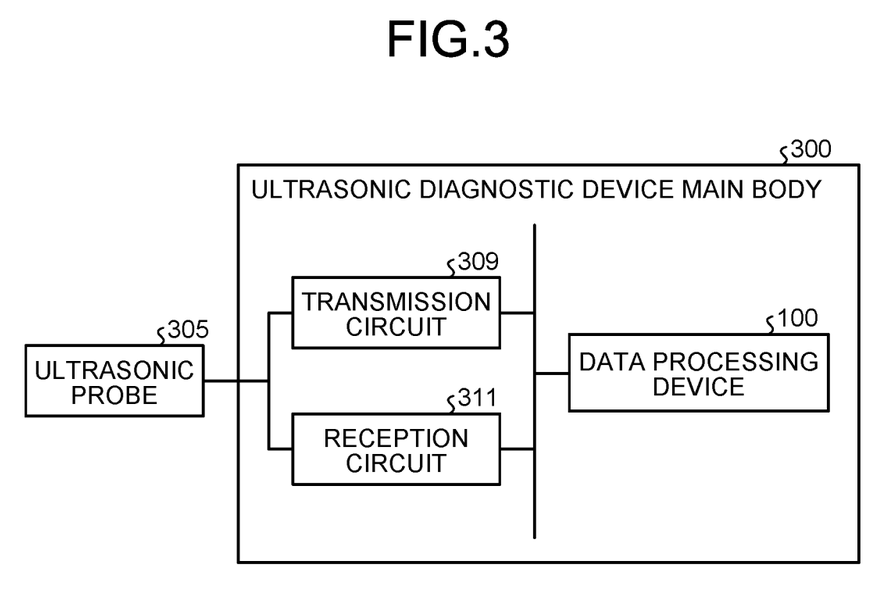
FIG. 3 is a diagram illustrating an example of an ultrasonic diagnostic device according to the embodiment.

FIG. 3 is a configuration example of an ultrasonic diagnostic device main body 300 incorporated with the data processing device 100 according to the embodiment. The ultrasonic diagnostic device according to the embodiment includes an ultrasonic probe 305 and the ultrasonic diagnostic device main body 300. The ultrasonic diagnostic device main body 300 includes a transmitter circuit 309, a receiver circuit 311, and the data processing device 100 described above.

The ultrasonic probe 305 has a plurality of piezoelectric transducer elements. The piezoelectric transducer elements generate ultrasonic waves on the basis of a drive signal supplied from the transmitter circuit 309 included in the ultrasonic diagnostic device main body 300, which will be described below. The piezoelectric transducer elements in the ultrasonic probe 305 receive reflected waves from the subject P, and convert the received reflected waves into electrical signals (reflected wave signals). The ultrasonic probe 305 has a matching layer on the piezoelectric transducer element, a backing material that prevents the ultrasonic waves from propagating from the piezoelectric transducer element to the rear, and the like. The ultrasonic probe 305 is detachably connected to the ultrasonic diagnostic device main body 300. Moreover, the ultrasonic probe 305 is an example of a scanning unit.

When ultrasonic waves are transmitted from the ultrasonic probe 305 to the subject P, the transmitted ultrasonic waves are reflected successively by the discontinuous surface of the acoustic impedance in the body tissue of the subject P, received by the piezoelectric transducer elements of the ultrasonic probe 305, and are converted into reflected wave signals. The amplitude of the reflected wave signal depends on the difference in acoustic impedance on the discontinuous surface that reflects the ultrasonic waves. When the transmitted ultrasonic pulse is reflected by the moving blood flow or the surface of the heart wall or the like, the reflected wave signal depends on the velocity component of the moving body with respect to the ultrasonic wave transmission direction due to Doppler effect, and undergoes a frequency shift.

The ultrasonic diagnostic device main body 300 is a device that generates ultrasonic image data on the basis of the reflected wave signal received from the ultrasonic probe 305. The ultrasonic diagnostic device main body 300 is a device capable of generating two-dimensional ultrasonic image data on the basis of a two-dimensional reflected wave signal, and that is capable of generating three-dimensional ultrasonic image data on the basis of a three-dimensional reflected wave signal. However, the embodiment is applicable even if the ultrasonic diagnostic device is a device dedicated to two-dimensional data.

As illustrated in FIG. 3, the ultrasonic diagnostic device 10 includes the transmitter circuit 309, the receiver circuit 311, and the data processing device 100.

The transmitter circuit 309 and the receiver circuit 311 control the ultrasonic transmission and reception performed by the ultrasonic probe 305, on the basis of the instruction of the data processing device 100 with a control function. The transmitter circuit 309 includes a pulse generator, a transmission delay unit, a pulser, and the like, and supplies a drive signal to the ultrasonic probe 305. The pulse generator repeatedly generates a rate pulse for forming transmission ultrasonic waves at a certain pulse repetition frequency (PRF). Moreover, the transmission delay unit provides a delay time of each piezoelectric transducer element necessary for focusing the ultrasonic waves generated from the ultrasonic probe 305 into a beam shape and for determining the transmission directivity, to each rate pulse generated by the pulse generator. Furthermore, the pulser applies a drive signal (drive pulse) to the ultrasonic probe 305 at a timing based on the rate pulse.

That is, the transmission delay unit optionally adjusts the transmission direction of the ultrasonic waves transmitted from the piezoelectric transducer element surface, by changing the delay time provided to each rate pulse. Moreover, the transmission delay unit controls the position of the focusing point (transmission focus) in the depth direction of the ultrasonic wave transmission, by changing the delay time provided to each rate pulse.

Furthermore, the receiver circuit 311 includes an amplifier circuit, an analog/digital (A/D) converter, a reception delay circuit, an adder, a quadrature detection circuit, and the like, and generates a reception signal (reflected wave data), by performing various processes on the reflected wave signal received from the ultrasonic probe 305. The amplifier circuit performs gain correction processing by amplifying the reflected wave signal for each channel. The A/D converter performs A/D conversion on the gain-corrected reflected wave signal. The reception delay circuit provides a reception delay time necessary for determining the reception directivity to digital data. The adder performs addition processing on the reflected wave signal to which the reception delay time is given by the reception delay circuit. The addition processing of the adder emphasizes the reflected component from the direction corresponding to the reception directivity of the reflected wave signal. Then, the quadrature detection circuit converts the output signal of the adder into an in-phase signal (I signal, I: In-phase) and a quadrature signal (Q signal, Q: Quadrature-phase) in the baseband. Then, the quadrature detection circuit transmits the I signal and Q signal (hereinafter referred to as IQ signals) to the processing circuit 110 as reception signals (reflected wave data). The quadrature detection circuit may also convert the output signal of the adder into a radio frequency (RF) signal and transmit the RF signal to the processing circuit 110. The IQ signal and the RF signal will be reception signals with phase information.

To scan a two-dimensional region in the subject P, the transmitter circuit 309 causes the ultrasonic probe 305 to transmit an ultrasonic beam for scanning the two-dimensional region. Then, the receiver circuit 311 generates a two-dimensional reception signal from the two-dimensional reflected wave signal received from the ultrasonic probe 305. Moreover, to scan a three-dimensional region in the subject P, the transmitter circuit 309 causes the ultrasonic probe 305 to transmit an ultrasonic beam for scanning the three-dimensional region. Then, the receiver circuit 311 generates a three-dimensional reception signal from the three-dimensional reflected wave signal received from the ultrasonic probe 305. The receiver circuit 311 generates a receive signal on the basis of the reflected wave signal, and transmits the generated reception signal to the processing circuit 110.

The transmitter circuit 309 causes the ultrasonic probe 305 to transmit an ultrasonic beam from a predetermined transmission position (transmission scanning line). At a predetermined reception position (reception scanning line), the receiver circuit 311 receives a signal based on the reflected wave of the ultrasonic wave beam transmitted from the transmitter circuit 309, from the ultrasonic probe 305. In the case of not performing parallel simultaneous reception, the transmission scanning line and the reception scanning line become the same scanning line. On the other hand, in the case of performing parallel simultaneous reception, when the transmitter circuit 309 causes the ultrasonic probe 305 to transmit one ultrasonic beam through one transmission scanning line, the receiver circuit 311 simultaneously receives the signal based on the reflected wave derived from the ultrasonic wave transmitted to the ultrasonic probe 305 by the transmitter circuit 309 at a plurality of predetermined reception positions (reception scanning lines) as a plurality of reception beams via the ultrasonic probe 305.

The data processing device 100 is connected to the transmitter circuit 309 and the receiver circuit 311. In addition to the functions already illustrated in FIG. 1, the data processing device 100 performs processing such as processing a signal received from the receiver circuit 311, controlling the transmitter circuit 309, generating a learned model, executing the learned model, and executing various image processing. In addition to the functions already illustrated in FIG. 1, the processing circuit 110 includes a B-mode processing function, a Doppler processing function, a generation function, and the like.

Subsequently, with reference to FIG. 4 and FIG. 5, a configuration of a neural network according to the embodiment will be described.

Figure 4:
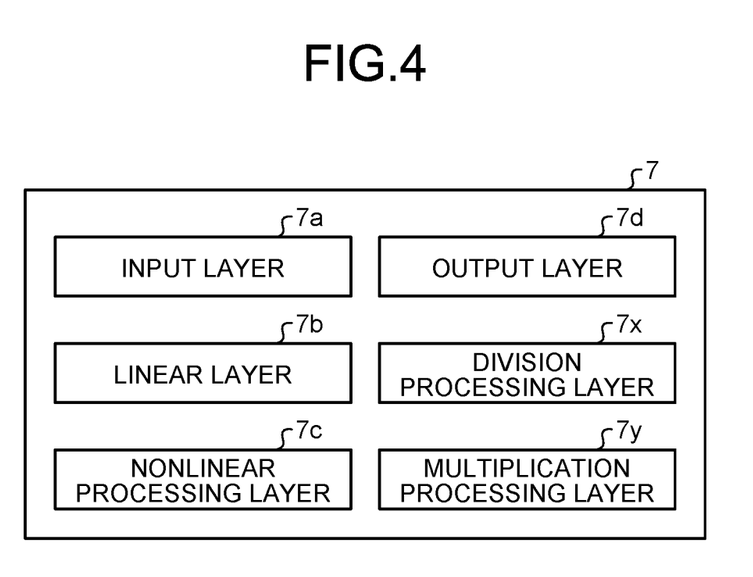
FIG. 4 is a diagram illustrating an example of a neural network according to the embodiment.
Figure 5:
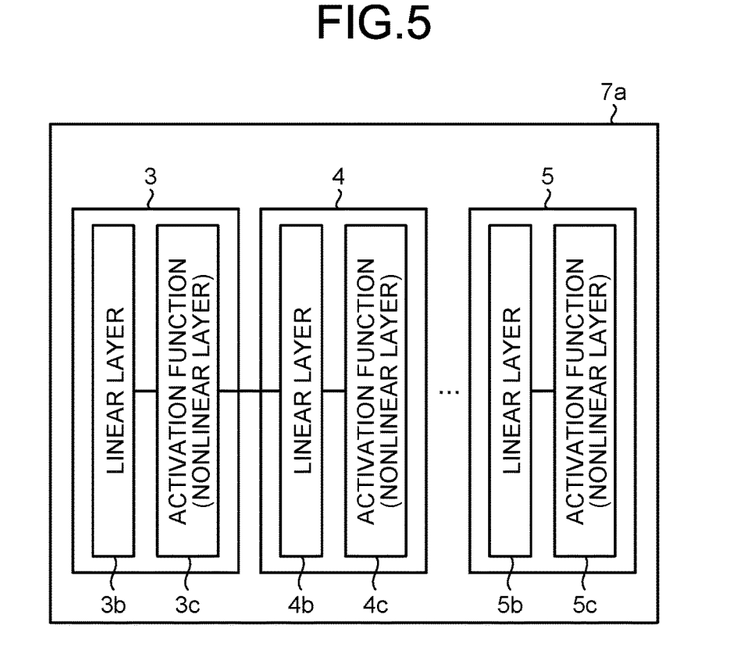
FIG. 5 is a diagram for explaining a neural network according to the embodiment.

FIG. 4 illustrates a configuration of a neural network 7 included in the learned model according to the embodiment. As illustrated in FIG. 4, the neural network 7 according to the embodiment includes an input layer 7a, a linear layer 7b, a nonlinear processing layer 7c, an output layer 7d, a division processing layer 7x, and a multiplication processing layer 7y. The neural network 7 according to the embodiment is configured by combining a plurality of the layers as appropriate. The data input to the input layer 7a is typically vector data, in other words, an input vector. The input vector is input to an intermediate layer of the neural network 7. Moreover, the data output to the output layer 7d is typically vector data, in other words, an output vector. The output vector is output from the intermediate layer of the neural network 7. The neural network 7 according to the embodiment includes the division processing layer 7x and the multiplication processing layer 7y compared to a general neural network 7a in FIG. 5, which will be described below. A detailed explanation of these points is given below.

Subsequently, with reference to FIG. 5, a typical configuration of the neural network will be described. FIG. 5 illustrates an example of the interconnections between layers in the neural network 7a generally used for machine learning. The neural network 7a typically includes an input layer, an output layer, and intermediate layers 3, 4, 5, and the like between the input layer and the output layer.

In this example, each intermediate layer includes a linear layer and a layer according to the processing using nonlinear processing (hereinafter referred to as an activation layer or a nonlinear layer). For example, the intermediate layer 3 includes a linear layer 3b and a nonlinear layer 3c. The intermediate layer 4 includes a linear layer 4b and a nonlinear layer 4c. The intermediate layer 5 includes a linear layer 5b and a nonlinear layer 5c. Moreover, each layer includes multiple nodes (neurons).

In this example, to the complex-valued medical data, the data processing device 100 according to the embodiment applies a linear layer with a complex number coefficient and nonlinear activation (activation function).

That is, in each layer, the processing circuit 110 includes a linear layer that performs a linear operation on an input vector input to each layer, and a nonlinear operation layer that performs a nonlinear operation on the output result of the linear layer. For example, in a case of the intermediate layer 5, that is the n-th layer, the intermediate layer 5 includes the linear layer 5b and the nonlinear layer 5c.

In this example, the linear layer performs a linear operation on the input data that is input to each layer. For example, if the number of elements of the input vector input to the intermediate layer 5, that is, the n-th layer is $m_n$, and the i-th element is the complex number $z_{n,i}$, the linear layer 5b outputs a vector in which the j-th element is the complex number $\sum_{i=1}^{m\_n} \omega_{n,i,j} z_{n,i} + b_{n,j}$, wherein j is a natural number.

In this example, $\omega_{n,i,j}$ is a weighting coefficient in the n-th linear layer, and is a certain constant known as a bias term.

Subsequently, the nonlinear layer applies a nonlinear function to the output result of the linear layer. As an example, the nonlinear layer 5c applies an activation function f to the output result of the linear layer 5b, and inputs the output result to the n+1-th layer, that is, the next layer. For example, when the activation function $f_{n,j}$, that is, the nonlinear function to be applied is used, the output result $z_{n+1,j}$ in the nonlinear layer 5c is expressed by the following formula (1).

$$z_{n+1,j} = f_{n,j}\left(\sum_{i=1}^{m\_n} \omega_{n,i,j} z_{n,i} + b_{n,j}\right) \quad (1)$$

In this manner, in each layer of the neural network 7, the final output result is obtained by applying the linear layer with a complex number coefficient and nonlinear activation (activation function) to the medical data with a complex value, and by sequentially outputting the results to the next layer.

Returning to FIG. 5, with the learning function 110b, the processing circuit 110 generates a learned model by training the neural network 7 that applies the linear layer with a complex number coefficient and the nonlinear function to the complex-valued medical data, using a method, which will be described below. For example, the processing circuit 110 stores the generated learned model in the memory 132 as necessary.

The input vector is typically a medical image or medical image data acquired from a medical image diagnostic device. For example, if the medical image diagnostic device is the magnetic resonance imaging apparatus 200, the input vector is a magnetic resonance image. Moreover, for example, if the medical image diagnostic device is the ultrasonic diagnostic device main body 300, the input vector is an ultrasonic image.

Furthermore, the input vector may be a medical image, or various image data, projection data, intermediate data, or raw data before the medical image is generated.

Still furthermore, for example, the output vector may be a medical image or medical image data, and similar to the input vector, the output vector may also be various projection data, intermediate data, or raw data before the medical image is generated. For example, if an object of the neural network 7 is to perform denoising, the data output from the output layer 2 is a high quality image from which noise is removed, compared to the input image. The processing circuit 110 outputs complex vector data as the output vector.

If the neural network 7 according to the embodiment is a convolutional neural network (CNN), for example, the input vector is data represented by a two-dimensional array of size 32×32 or the like, and for example, the output vector is data represented by a two-dimensional array of size 32×32 or the like. The size of the input vector and the size of the output vector may be the same or different. Similarly, the size of the output vector in the intermediate layer may be the same or different from the size of the input vector in the intermediate layer.

Subsequently, generation of the learned model according to the embodiment, that is, a learning step will be described. For example, with the learning function 110b, the processing circuit 110 generates a learned model by carrying out machine learning on the neural network 7. In this example, to carry out machine learning means to determine the weights in the neural network 7 including the input layer, the intermediate layers 3, 4, and 5, and the output layer, for example. More specifically, to carry out machine learning means to determine a set of coefficients that characterizes the connection between the input layer and the intermediate layer 3, a set of coefficients that characterizes the connection between the intermediate layer 3 and the intermediate layer 4, . . . , and a set of coefficients that characterizes the connection between the intermediate layer 5 and the output layer. For example, with the learning function 110*b*, the processing circuit 110 determines these sets of coefficients, using a back propagation method.

With the learning function 110*b*, the processing circuit 110 carries out machine learning on the basis of training data that is supervised data including the input vector and the output vector, determines the weights between the layers, and generates a learned model in which the weights are determined.

In deep learning, self-encoding (autoencoder) can be used. In this case, the data required for machine learning need not be supervised data.

Subsequently, a process of applying the learned model according to the embodiment will be described. First, for example, with the application function 110*e*, the processing circuit 110 inputs an input medical image, that is, a clinical image to the learned model. For example, with the application function 110*e*, the processing circuit 110 inputs an input medical image, that is, a clinical image to the input layer of the neural network 7, that is, the learned model. Subsequently, with the application function 110*e*, the processing circuit 110 obtains the data output from the output layer of the neural network 7, that is, the learned model, as an output medical image. For example, the output medical image is a medical image on which a predetermined process such as noise removal is performed. In this manner, for example, with the application function 110*e*, the processing circuit 110 generates the output medical image on which a predetermined process such as noise removal is performed. As necessary, with the control function 110*d*, the processing circuit 110 may also display the acquired output medical image on the display 135.

Subsequently, the background according to the embodiment will be described.

In machine learning using a neural network, a real-valued neural network is used as a standard. However, in the medical data processing device such as a magnetic resonance imaging apparatus and an ultrasonic diagnostic device, signal processing using complex numbers is often used. Hence, various applications are possible by using a complex-valued neural network.

In this example, for example, in a medical image such as a magnetic resonance image and an ultrasonic image, while the phase information of an image, for example, the gradient of the phase, is often important, the absolute value of the phase seldom has significant implications. For example, in the magnetic resonance imaging apparatus, a slight difference in the center frequency appears as a phase modulation of the entire image. However, in many cases, the importance of the absolute values of the phases is relatively low.

Thus, for example, when the complex-valued neural network is applied to a medical image for noise removal, region extraction, and the like, it is desirable to configure the neural network such that the output result does not vary significantly with respect to the phase modulation of the entire image, while the phase information of the input image is not ignored.

In view of such a background, in the neural network 7, the data processing device 100 according to the embodiment includes the division processing layer that performs division by multiple vector data containing the features of the input data during learning, and a multiplication processing layer that performs multiplication by the multiple vector data. The data processing device 100 applies scaling with complex numbers before and after activation in the neural network 7. As a result, it is possible to improve the learning stability on the change in phase and the change in magnification of signal values.

Figure 6:
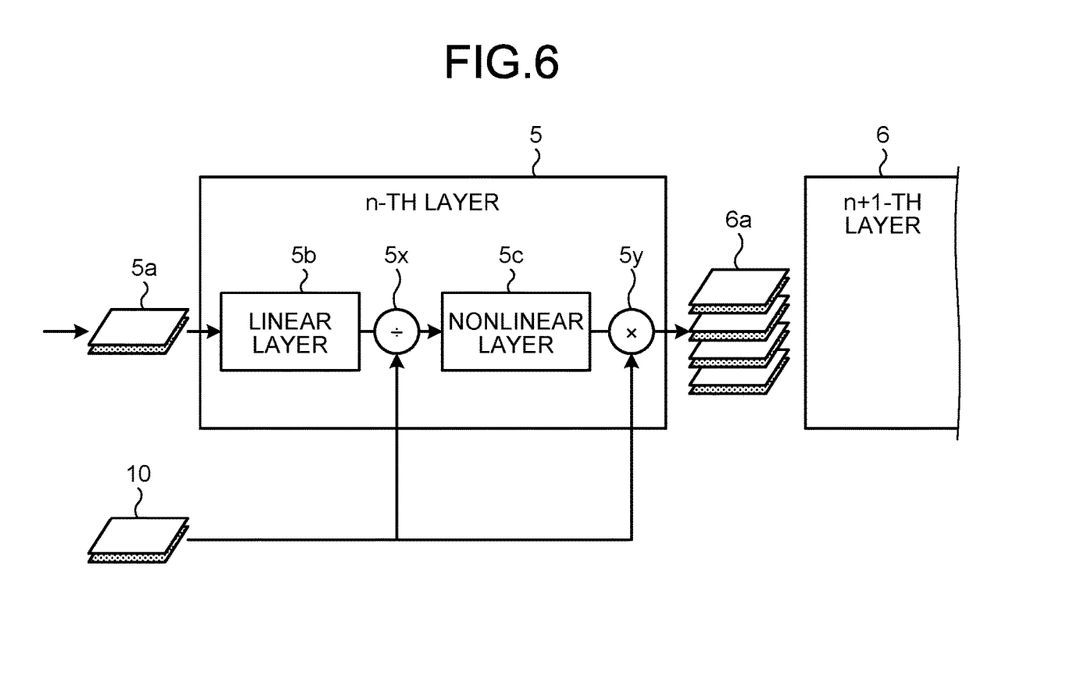
FIG. 6 is a diagram illustrating an example of a configuration of a data processing device according to a first embodiment.

Such a configuration will be described with reference to FIG. 6. FIG. 6 is a diagram illustrating an example of a configuration of the data processing device 100 according to the embodiment including a neural network according to the learned model. In the neural network according to the learned model according to the embodiment, the complex first vector data is the input data during learning. For example, the complex first vector data is a magnetic resonance imaging image of a complex value obtained based on collected data collected by a magnetic resonance imaging apparatus.

As illustrated in FIG. 6, the intermediate layer 5, that is, the n-th layer of the neural network 7 according to the embodiment performs a linear operation on an input vector 5*a* to which the output result from the n−1-th layer is input. The intermediate layer 5 includes the linear layer 5*b* disposed in the preceding stage of a division processing layer 5*x*, the division processing layer 5*x* disposed in the subsequent stage of the linear layer 5*b*, the nonlinear layer 5*c* disposed in the subsequent stage of the division processing layer, and a multiplication processing layer 5*y* disposed in the subsequent stage of the nonlinear layer 5*c*. The output result of the output unit of the division processing layer of the n−1-th layer becomes the input vector 5*a*, and the output result of the output unit of the multiplication processing layer 5*y* becomes an input vector 6*a* of the n+1-th layer.

Moreover, the complex first vector data, that is, the input data during learning, is input to the first layer, and the output result is output from the output layer of the final layer. Furthermore, the division processing layer 5*x* and the multiplication processing layer 5*y* are connected to second vector data 10 that is the second vector data containing the features of the complex first vector data, that is, the input data during learning.

The input vector 5*a*, the second vector data 10, and the like are complex number data. However, for example, the data of the real part and the data of the imaginary part may be held separately as separate data.

Subsequently, the process in the n-th layer will be described. First, the data output from the n−1-th layer is input as the input vector 5*a*. Typically, the data output from the division processing layer 5*a* of the n−1-th layer is output as the input vector 5*a*. For example, the input vector 5*a* is complex vector data. Subsequently, the linear layer 5*b* performs a linear operation on the input data that is input to the n-th layer, that is, the input vector 5*a*.

Subsequently, the division processing layer 5*x* divides the output result of the linear layer 5*b* by the complex second vector data 10 containing the features of the input data during learning. That is, the division processing layer 5*x* divides the input complex first vector data by the complex second vector data containing the features of the first vector data. In this example, the second vector data 10 includes maps such as a sensitivity map, a B0 (static magnetic field) map, a B1 (high frequency magnetic field) map, and a noise map. That is, examples of the second vector data 10 include maps that represent the features of the sensitivity map, B0 map, B1 map, noise map, and the like, and maps represented by complex numbers. However, examples of the second vector data 10 also include the sensitivity map, B0 map, B1 map, noise map, and the like that are used without any change. As the second vector data 10, the complex vector data is basically selected. For example, the second vector data is typically data including a phase component or an intensity component that correlates with the first vector data.

The meaning of the division processing layer 5x performing scaling by dividing with the second vector data 10 will now be described. By performing such a process, it is possible to cancel the phase component included in the second vector data 10 from the first vector data of the input data, extract the phase component of the first vector data relative to the phase component included in the second vector data, and learn the phase component. As a result, it is possible to improve the learning stability of the neural network 7 on the phase. Similarly, by dividing the second vector data 10, it is possible to extract the intensity of the amplitude component of the first vector data relative to the amplitude component of the second vector data, and learn the relative intensity. In other words, the division processing layer 5x normalizes the phase or intensity of the first vector data by the division process. As a result, it is possible to improve the learning stability on the input data during learning.

Subsequently, the nonlinear layer 5c performs activation by performing a nonlinear operation on the output result of the division processing layer 5x by applying a nonlinear function. An example of the nonlinear function used in this example is represented by the following function, for example.

$$f(z)=\text{ReLU}(\text{Re}(z))+i^*\text{ReLU}(\text{Im}(z)) \quad (2)$$

By applying ReLU to each of the real part and the imaginary part, it is possible to assume that this function is obtained by expanding the nonlinear function ReLU defined for the real number into the complex number.

The method of expanding the nonlinear function defined for the real number into the complex number is not limited to the above. For example, it is also possible to expand the nonlinear real function into the complex number, by applying the nonlinear function only on the real part, or applying the nonlinear function to the absolute value portion of the complex number. That is, the nonlinear layer 5c includes the function obtained by expanding the nonlinear real function into the complex number.

Moreover, the function to be expanded is not limited to ReLU, and may also be obtained by expanding a generally known activation function such as LeakyReLU, ELU, CELU, GELU, SELU, Swish, SoftShrink, HardShrink, Sigmoid, and TanhShrink. Furthermore, the domain of the functions may be shifted, or a part or all constants that characterize the functions may be replaced with learnable parameters.

Subsequently, the multiplication processing layer 5y multiplies the output result of the nonlinear layer 5c by the second vector data to calculate a complex feature map. In this manner, the data on which scaling is performed by the division processing layer is restored by the multiplication processing layer. The multiplication processing layer 5y outputs the complex feature map, that is the result of multiplication, as the output data of the n-th layer, and inputs the output data to the n+l-th layer as the input vector 6a. The embodiment is not limited to the example described above. For example, a BatchNormalization layer may be provided between the division processing layer 5x and the nonlinear layer 5c, or a Dropout layer may be provided subsequent to the nonlinear layer 5c or subsequent to the multiplication processing layer 5y.

In this manner, the data processing device 100 according to the first embodiment performs scaling on the input data by the division processing layer. As a result, it is possible to improve the learning stability on the phase and amplitude of the input data during learning, and improve the image quality of the output image.

Second Embodiment

In the embodiment described above, the second vector data 10 that is data used for scaling is provided in advance. However, the embodiment is not limited thereto. In the second embodiment, the second vector data is obtained as an output result of another neural network.

Figure 7:
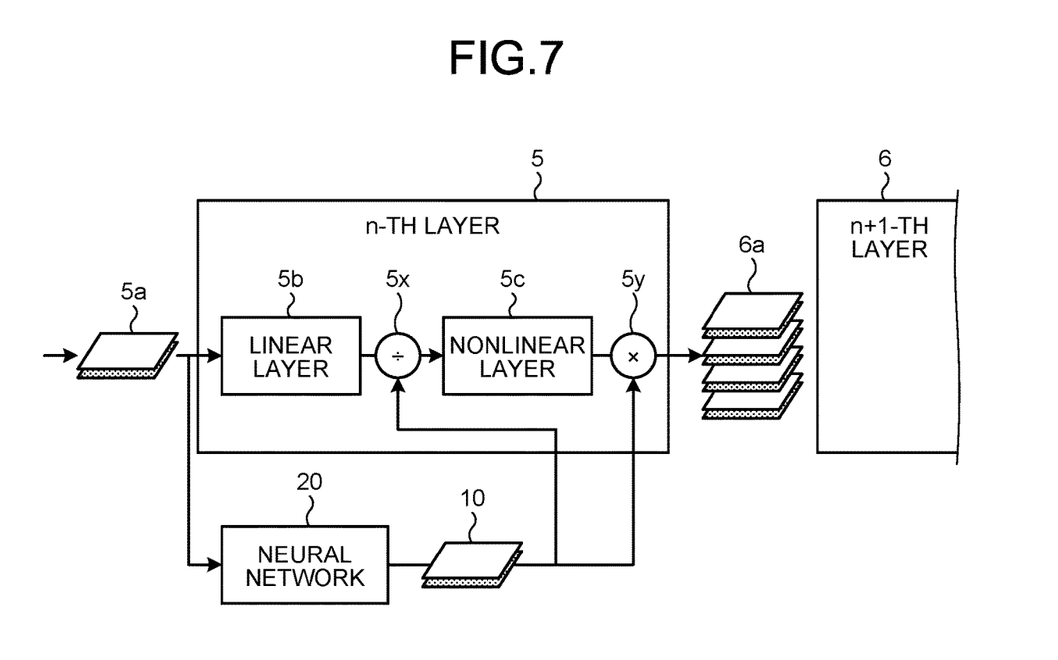
FIG. 7 is a diagram illustrating an example of a configuration of a data processing device according to a second embodiment.

FIG. 7 illustrates an example of such a configuration. In the second embodiment, there is a second neural network 20 that is different from the neural network 7 including the intermediate layer 5, an intermediate layer 6, and the like. In this example, the neural network 20 may or may not include a learning parameter. However, the neural network 20 is preferably a linear network without a nonlinear operation and a bias term.

In this example, the input vector 5a is input to the input side of the neural network 20, and the second vector data 10 is output from the output side of the neural network 20. That is, in the second embodiment, the input vector 5a is input to the second neural network 20, and the second vector data 10, that is, data used for scaling is generated as the output result of the second neural network 20. That is, in the second embodiment, the second vector data 10 is the output data obtained by inputting input data to the second neural network 20 that is different from the neural network 7.

The second neural network 20 may be the same neural network for each layer in the neural network 7, or may be a neural network in which the internal parameter changes with each layer.

In this manner, in the second embodiment, the scaling is performed on the basis of the second vector data generated by the other neural network. As a result, it is possible to perform scaling in a flexible manner according to the characteristics of the input data, and improve the image quality.

Third Embodiment

Figure 8:
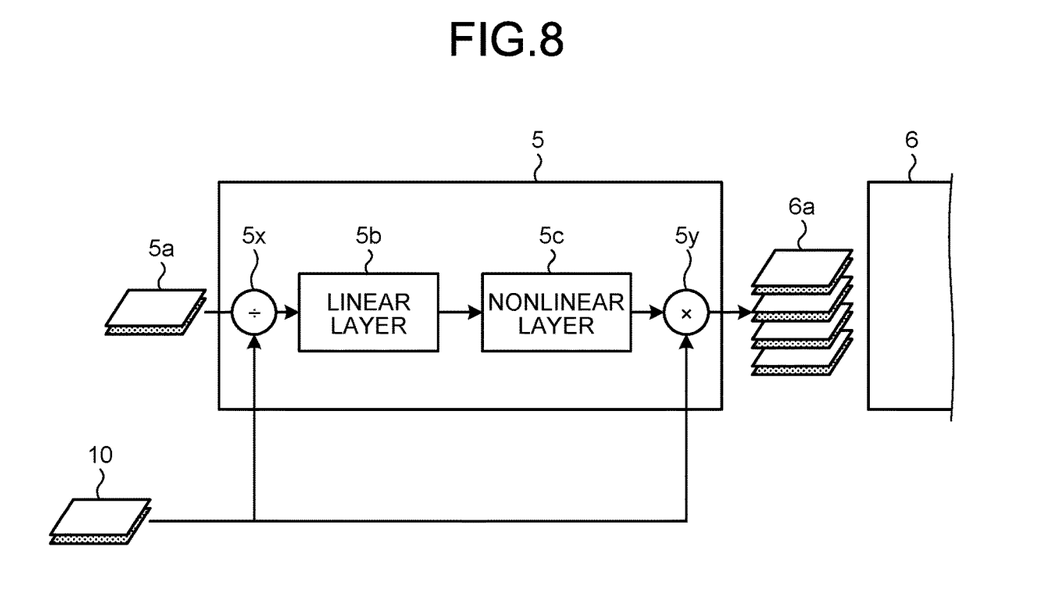
FIG. 8 is a diagram illustrating an example of a configuration of a data processing device according to a third embodiment.

The embodiment is not limited to the example described above, and many variations of the embodiment are possible. As an example, in the first embodiment, the division processing layer 5x is disposed subsequent to the linear layer 5b. However, the embodiment is not limited thereto. For example, in the third embodiment, as illustrated in FIG. 8, the division processing layer 5x is disposed in front of the linear layer 5b. That is, in the third embodiment, the linear layer 5b is disposed in the subsequent stage of the division processing layer 5x, and is disposed in the preceding stage of the multiplication processing layer 5y.

That is, each layer in the neural network 7 of the learned model according to the third embodiment includes the division processing layer 5x to which the input vector 5a is input, the linear layer 5b disposed in the subsequent stage of the division processing layer 5x, the nonlinear layer 5c disposed in the subsequent stage of the linear layer 5b, and the multiplication processing layer 5y disposed in the subsequent stage of the nonlinear layer 5c. The division processing layer 5x divides the input data that is input to the input layer 5a in each layer by the second vector data. The linear layer 5b performs a linear operation on the output result of the division processing layer 5x. The nonlinear layer 5c performs a nonlinear operation on the output result of the linear layer 5b. The multiplication processing layer 5y multiplies the output result of the nonlinear layer 5c by the second vector data 10, and outputs the result of multiplication as the output data of the layer.

In this manner, in the third embodiment, it may be possible to improve the image quality of the output image, by disposing the division processing layer 5x in the preceding stage of the linear layer 5b.

Fourth Embodiment

The embodiment is not limited to the example described above. In the first embodiment, the division and multiplication using the second vector data are performed in each layer. However, the embodiment is not limited thereto. The division process and the multiplication process using the second vector data 10 may only be performed once in each of the first layer and the last layer.

Figure 9:
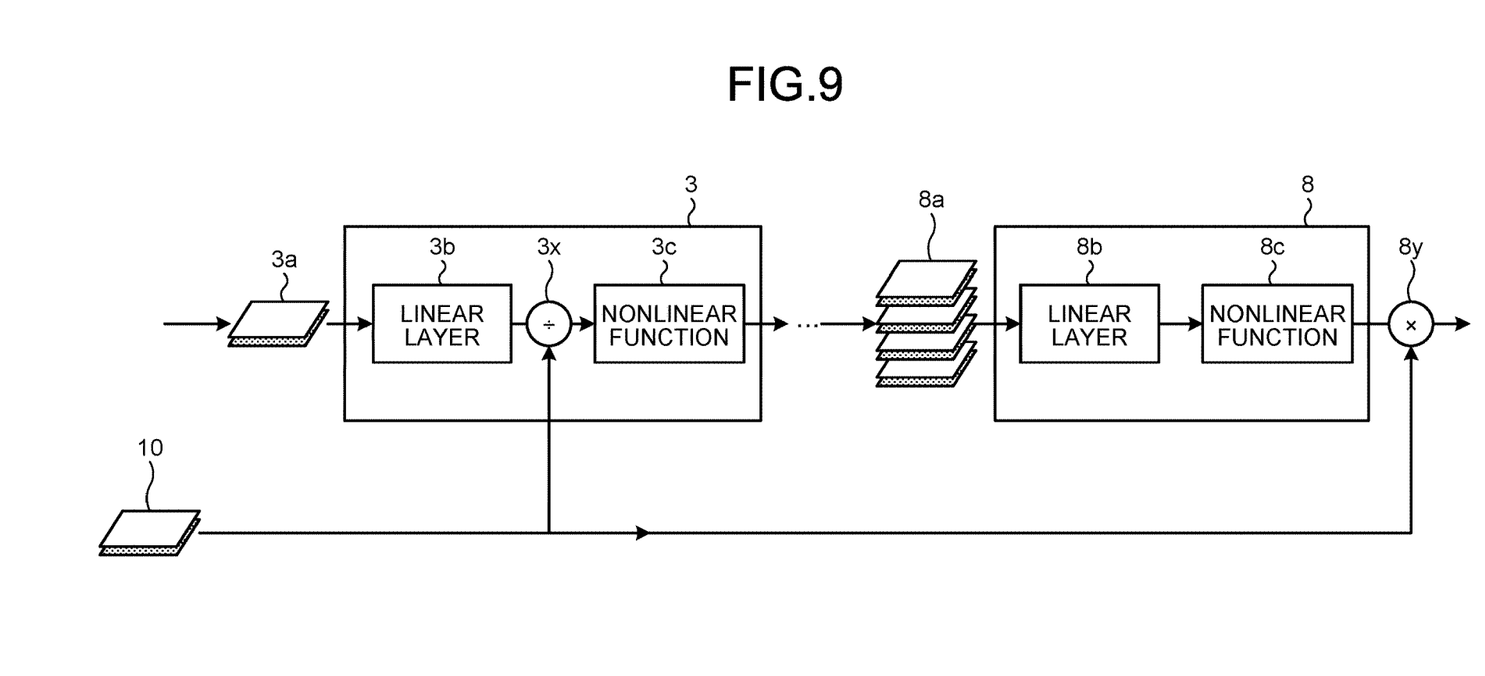
FIG. 9 is a diagram illustrating an example of a configuration of a data processing device according to a fourth embodiment.

FIG. 9 illustrates such a situation. In FIG. 9, the intermediate layer 3 represents the foremost layer among the layers of the neural network 7, and an intermediate layer 8 represents the last layer among the layers of the neural network 7. The intermediate layer 3 includes the linear layer 3b to which an input vector 3a is input, a division processing layer 3x, and the nonlinear layer 3c. The intermediate layer 8 includes a linear layer 8b to which an input vector 8a is input, a nonlinear function 8c, and a multiplication processing layer 8y. That is, the division processing layer 3x is disposed in the frontmost layer among the layers of the neural network 7, and the multiplication processing layer 8y is disposed in the last layer among the layers of the neural network.

In this manner, in the fourth embodiment, the division processing layer 3x is disposed in the foremost layer and the multiplication processing layer 8y is disposed in the last layer. By performing the process only once in the division processing layer 3x and the multiplication processing layer 8y, it is possible to reduce the calculation load.

Fifth Embodiment

Figure 10:
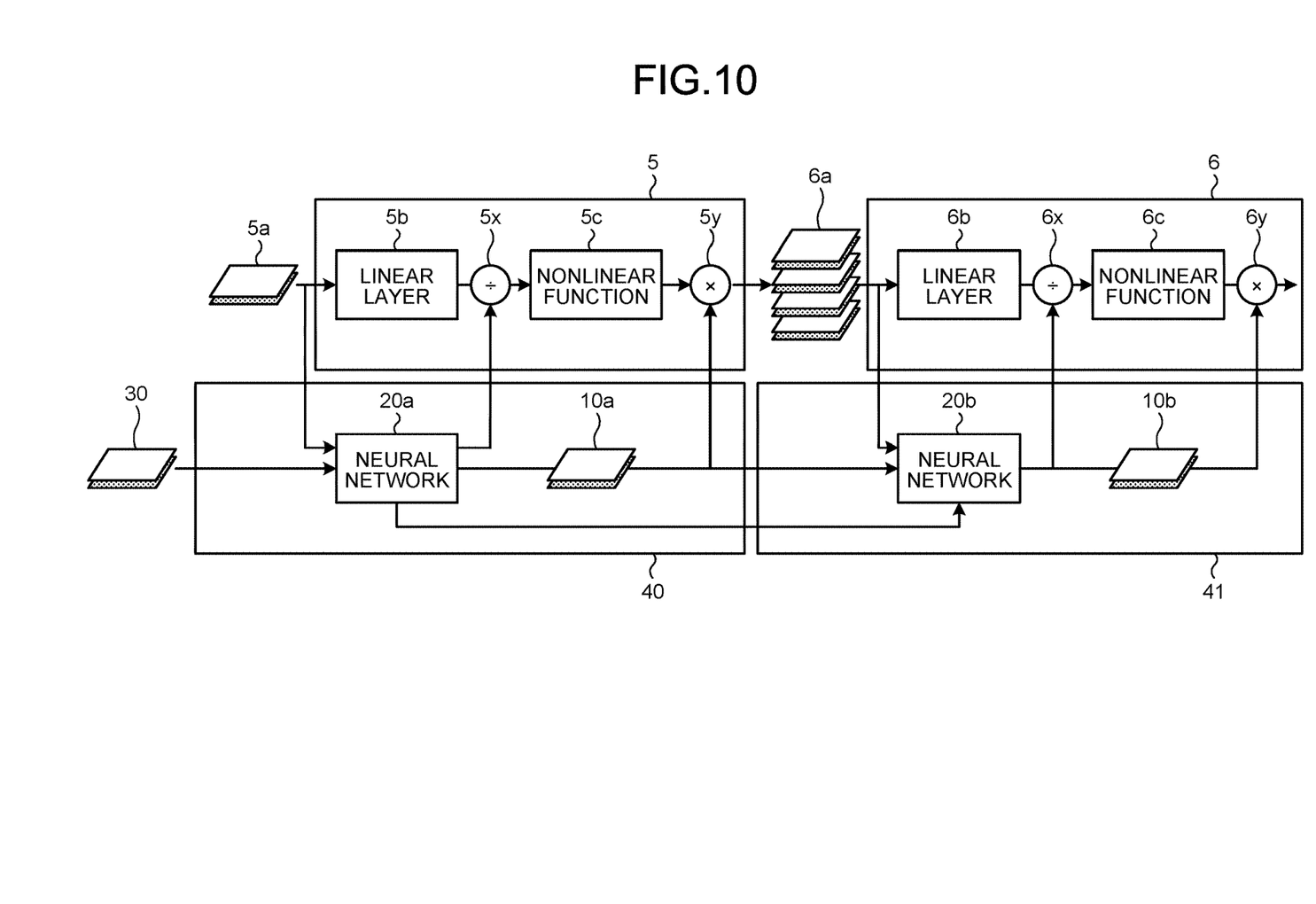
FIG. 10 is a diagram illustrating an example of a configuration of a data processing device according to a fifth embodiment.

In the fifth embodiment, the second vector data that is data used for scaling, is generated on the basis of third vector data that is separate data. FIG. 10 is a diagram illustrating an example of a configuration of the neural network 7 according to the fifth embodiment.

The third vector data 30 is data for generating second vector data 10a, 10b, and the like that are data used for scaling. For example, the third vector data 30 is data on a map of sensitivity, B0, or noise, and the like. The third vector data 30 may also be the first vector data, or may also be data generated using multiple data among maps of the first vector data, sensitivity, B0, B1, or noise. Moreover, neural networks 20a and 20b are neural networks themselves, and output data according to the input of certain data. For example, the neural network 20a outputs the second vector data 10a on the basis of the input vector 5a and the third vector data. Moreover, the neural network 20b outputs the second vector data 10b on the basis of the input vector 6a, the second vector data 10a, and the input from the neural network 20a.

Furthermore, the division processing layer 5x divides the output result from the linear layer 5b by the second vector data 10a, and outputs the result of the division process to the nonlinear layer 5c. The multiplication processing layer 5y multiplies the output result of the nonlinear layer 5c by the second vector data 10b, and outputs the result of the multiplication process as the input vector 6a.

Similarly, a division processing layer 6x divides the output result from a linear layer 6b by the second vector data 10b, and outputs the result of the division process to a nonlinear layer 6c. A multiplication processing layer 6y multiplies the output result of the nonlinear layer 6c by the second vector data 10b, and outputs the result of the multiplication process.

As described above, in the fifth embodiment, the second vector data is the output data obtained by inputting the input data obtained from the third vector data 30, to the second neural network that is different from the neural network 7. In this manner, by making the second vector data that is data used for scaling as the output result of the neural network for each layer, it is possible to change the second vector data in each layer, and perform scaling in a flexible manner.

According to at least one of the embodiments described above, it is possible to improve the image quality.

In relation to the embodiments described above, the following notes are disclosed as aspects and selective characteristics of the invention.

Note 1. A data processing device provided in one aspect of the present invention includes a processing circuit that performs data processing using a learned model with a neural network that includes a division processing layer that divides input complex first vector data by complex second vector data containing a feature of the first vector data, a nonlinear layer that is disposed in a subsequent stage of the division processing layer and that performs a nonlinear operation, and a multiplication processing layer that is disposed in a subsequent stage of the nonlinear layer and that multiplies the input data by the second vector data.

Note 2. The processing circuit may also output complex vector data.

Note 3. The neural network may also include a linear layer that performs a linear operation.

Note 4. The linear layer may also be disposed in a preceding stage of the division processing layer.

Note 5. The linear layer may also be disposed in a subsequent stage of the division processing layer and in a preceding stage of the multiplication processing layer.

Note 6. The second vector data may also be a map of sensitivity, B0, B1, or noise.

Note 7. The second vector data may also be data obtained by inputting input data to a second neural network that is different from the neural network.

Note 8. The division processing layer may also be disposed in the foremost layer among layers of the neural network, and
the multiplication processing layer may also be disposed in the last layer among the layers of the neural network.

Note 9. The second vector data may also be output data obtained by inputting input data obtained from third vector data, to a second neural network that is different from the neural network.

Note 10. The third vector data may also be a map of the first vector data, sensitivity, B0, B1, or noise, or may be data generated using multiple data among maps of the first vector data, sensitivity, B0, B1, or noise.

Note 11. The learned model may also include a linear layer that performs a linear operation on input data, wherein the division processing layer may divide the output result of the linear layer by the second vector data, the nonlinear layer may perform the nonlinear operation on the output result of the division processing layer, and the multiplication processing layer may multiply the output result of the nonlinear layer by the second vector data, and output the result of multiplication as the output data of the layer.

Note 12. The learned model may also include a linear layer that performs a linear operation on input data, wherein the division processing layer may divide the input data that is input by the second vector data, the linear layer may perform the linear operation on the output result of the division processing layer, the nonlinear layer may perform the nonlinear operation on the output result of the linear layer, and the multiplication processing layer may multiply the output result of the nonlinear layer by the second vector data, and output the result of multiplication as the output data of the layer.

Note 13. The second vector data may also be data including a phase component or an intensity component that correlates with the first vector data.

Note 14. The division processing layer may also normalize the phase or intensity of the first vector data by a division process.

Note 15. The nonlinear layer may also include a function obtained by expanding a nonlinear real function into a complex number.

Note 16. A magnetic resonance imaging device provided in one aspect of the present invention includes a processing circuit that performs data processing using a learned model with a neural network that includes a division processing layer that divides input complex first vector data by complex second vector data containing a feature of the first vector data, a nonlinear layer that is disposed in a subsequent stage of the division processing layer and that performs a nonlinear operation, and a multiplication processing layer that is disposed in a subsequent stage of the nonlinear layer and that multiplies the input data by the second vector data.

Note 17. A data processing method provided in one aspect of the present invention performs data processing using a learned model with a neural network that includes a division processing layer that divides input complex first vector data by complex second vector data containing a feature of the first vector data, a nonlinear layer that is disposed in a subsequent stage of the division processing layer and that performs a nonlinear operation, and a multiplication processing layer that is disposed in a subsequent stage of the nonlinear layer and that multiplies the input data by the second vector data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A data processing device, comprising:
a processing circuit configured to perform data processing using a learned model with a neural network that includes
a division processing layer that divides input complex first vector data by complex second vector data containing a feature of the first vector data, the first vector data being input medical image data,
a nonlinear layer that is disposed in a stage subsequent to the division processing layer and that performs a nonlinear operation,
a multiplication processing layer that is disposed in a stage subsequent to the nonlinear layer and that multiplies data having passed through the nonlinear layer by the second vector data; and
an output layer that outputs output medical image data.

2. The data processing device according to claim 1, wherein the processing circuit is further configured to output complex vector data.

3. The data processing device according to claim 1, wherein the neural network further includes a linear layer that performs a linear operation.

4. The data processing device according to claim 3, wherein the linear layer is disposed in a stage preceding the division processing layer.

5. The data processing device according to claim 3, wherein the linear layer is disposed in a stage subsequent to the division processing layer and preceding the multiplication processing layer.

6. The data processing device according to claim 1, wherein
the division processing layer is disposed in a foremost layer among layers of the neural network, and
the multiplication processing layer is disposed in a last layer among the layers of the neural network.

7. The data processing device according to claim 1, wherein the second vector data is a map of sensitivity, B0, B1, or noise.

8. The data processing device according to claim 1, wherein the second vector data is data obtained by inputting input data to a second neural network that is different from the neural network.

9. The data processing device according to claim 1, wherein the second vector data is output data obtained by inputting input data obtained from third vector data, to a second neural network that is different from the neural network.

10. The data processing device according to claim 9, wherein the third vector data is a map of the first vector data, sensitivity, B0, B1, or noise, or data generated using multiple data among maps of the first vector data, sensitivity, B0, B1, or noise.

11. The data processing device according to claim 1, wherein the second vector data is data including a phase component or an intensity component that correlates with the first vector data.

12. The data processing device according to claim 1, wherein the division processing layer normalizes a phase or intensity of the first vector data by a division process.

13. The data processing device according to claim 1, wherein the nonlinear layer includes a function obtained by expanding a nonlinear real function into a complex number.

14. The data processing device according to claim 1, wherein the first vector data is medical image data obtained by an image diagnostic device.

15. The data processing device according to claim 14, wherein the image diagnostic device is a magnetic resonance imaging apparatus or an ultrasonic diagnostic device.

16. The data processing device of claim 1, wherein the processing circuit is further configured to control a display to display a noise-reduced medical image based on the output medical data, and the input medical image data is obtained by scanning a patient with a medical scanning apparatus.

17. The data processing device according to claim 1, wherein the multiplication processing layer multiplies data output from the nonlinear layer by the second vector data.

18. A magnetic resonance imaging apparatus, comprising:

a processing circuit configured to perform data processing using a learned model with a neural network that includes a division processing layer that divides input complex first vector data by complex second vector data containing a feature of the first vector data, the first vector data being input medical image data, a nonlinear layer that is disposed in a stage subsequent to the division processing layer and that performs a nonlinear operation, a multiplication processing layer that is disposed in a stage subsequent to the nonlinear layer and that multiplies data having passed through the nonlinear layer by the second vector data; and an output layer that outputs output medical image data.

19. A data processing method, comprising:

performing data processing using a learned model with a neural network that includes:

a division processing layer that divides input complex first vector data by complex second vector data containing a feature of the first vector data, the first vector data being input medical image data, a nonlinear layer that is disposed in a stage subsequent to the division processing layer and that performs a nonlinear operation, a multiplication processing layer that is disposed in a stage subsequent to the nonlinear layer and that multiplies data having passed through the nonlinear layer by the second vector data, and an output layer that outputs output medical image data.

\* \* \* \* \*